United States Patent
Kim et al.

(10) Patent No.: US 8,383,375 B2
(45) Date of Patent: Feb. 26, 2013

(54) THERMOSTABLE GLUCONATE DEHYDRATASE AND USE THEREOF

(75) Inventors: Seonghun Kim, Ulsan (KR); Sun Bok Lee, Pohang (KR)

(73) Assignees: Posco, Nam-gu, Kyungsangbuk-do, Pohang (KR); Postech Foundation, Hyoja-dong, Nam-gu, Kyungsangbuk-do, Pohang (KR)

( * ) Notice: Subject to any disclaimer, the term of this patent is extended or adjusted under 35 U.S.C. 154(b) by 76 days.

(21) Appl. No.: 12/910,768

(22) Filed: Oct. 22, 2010

(65) Prior Publication Data

US 2011/0111471 A1 May 12, 2011

Related U.S. Application Data (62) Division of application No. 11/568,848, filed as application No. PCT/KR2004/001126 on May 13, 2004, now abandoned.

(51) Int. Cl.
*C12P 7/58* (2006.01)
*C12P 7/42* (2006.01)
*C12P 7/50* (2006.01)
(52) U.S. Cl. .................. 435/137; 435/143; 435/146
(58) Field of Classification Search .............. None
See application file for complete search history.

(56) References Cited

FOREIGN PATENT DOCUMENTS

EP  0697461 A1  2/1996

OTHER PUBLICATIONS

She, Q. et al., "The complete genome of the crenarchaeon Sulfolobus solfataricus P2," Proc National Academy of Science USA, 98(14): 7835-7840 (2001).
Lamble, H.J. et al., "Metabolic pathway promiscuity in the archaeon Sulfolobus solfataricus revealed by studies on glucose dehydrogenase and 2-keto-3-deoxygluconate alsolase," The Journal of Biological Chemistry, 278 (36): 34066-34072 (2003).

*Primary Examiner* — Tekchand Saidha
*Assistant Examiner* — Md. Younus Meah
(74) *Attorney, Agent, or Firm* — Joseph Hyosuk Kim; JHK Law (57) ABSTRACT

The present invention relates to a novel thermostable gluconate dehydratase from the thermoacidophilic archaeon *Sulfolobus solfataricus*, a coding sequence, and an expression system. The gluconate dehydratase has a molecular weight of about 320,000 to 380,000 daltons as the native protein, and about 40,000 to 50,000 daltons as the monomer protein, and catalyzes the dehydration reaction of aldonic acids to 2-keto-3-deoxy derivatives at temperatures of less than 120° C. The gluconate dehydratase can be produced from native or recombinant host cells and thereby used in the pharmaceutical, agricultural, and other industries.

4 Claims, 5 Drawing Sheets

FIG. 5

THERMOSTABLE GLUCONATE DEHYDRATASE AND USE THEREOF

CROSS-REFERENCE TO RELATED APPLICATIONS

The present application is a divisional of U.S. patent application Ser. No. 11/568,848, filed Nov. 8, 2006 now abandoned, which is a national phase of PCT Application No. PCT/KR2004/001126, filed May 13, 2004, the contents of which are incorporated by reference herein in their entirety.

TECHNICAL FIELD

The present invention relates to a novel nucleic acid coding for a thermostable gluconate dehydratase from the archaeon *Sulfolobus solfataricus*, a novel polypeptide coded by the nucleic acid, and use thereof, as well as a method for preparing and isolating the recombinant gluconate dehydratase, and catalyzing aldonic acids to 2-keto-3-deoxy derivatives.

BACKGROUND ART

The hyperthermophilic archaea are microorganisms that grow optimally at a temperature above 80° C. Many species of these extremely thermophilic bacteria-like organisms have been isolated, mainly from volcanically and geothermally heated hydrothermal environments, such as solfataric fields, hot springs, and submarine hot vents.

The discovery of microorganisms growing optimally around 80° C. is of considerable interest in both academic and industrial communities. Both the organisms and their enzymes have the potential to bridge the gap between biochemical catalysis and many industrial chemical conversions. However, knowledge of the metabolism of the hyperthermophilic microorganisms is presently very limited.

Figure 1:
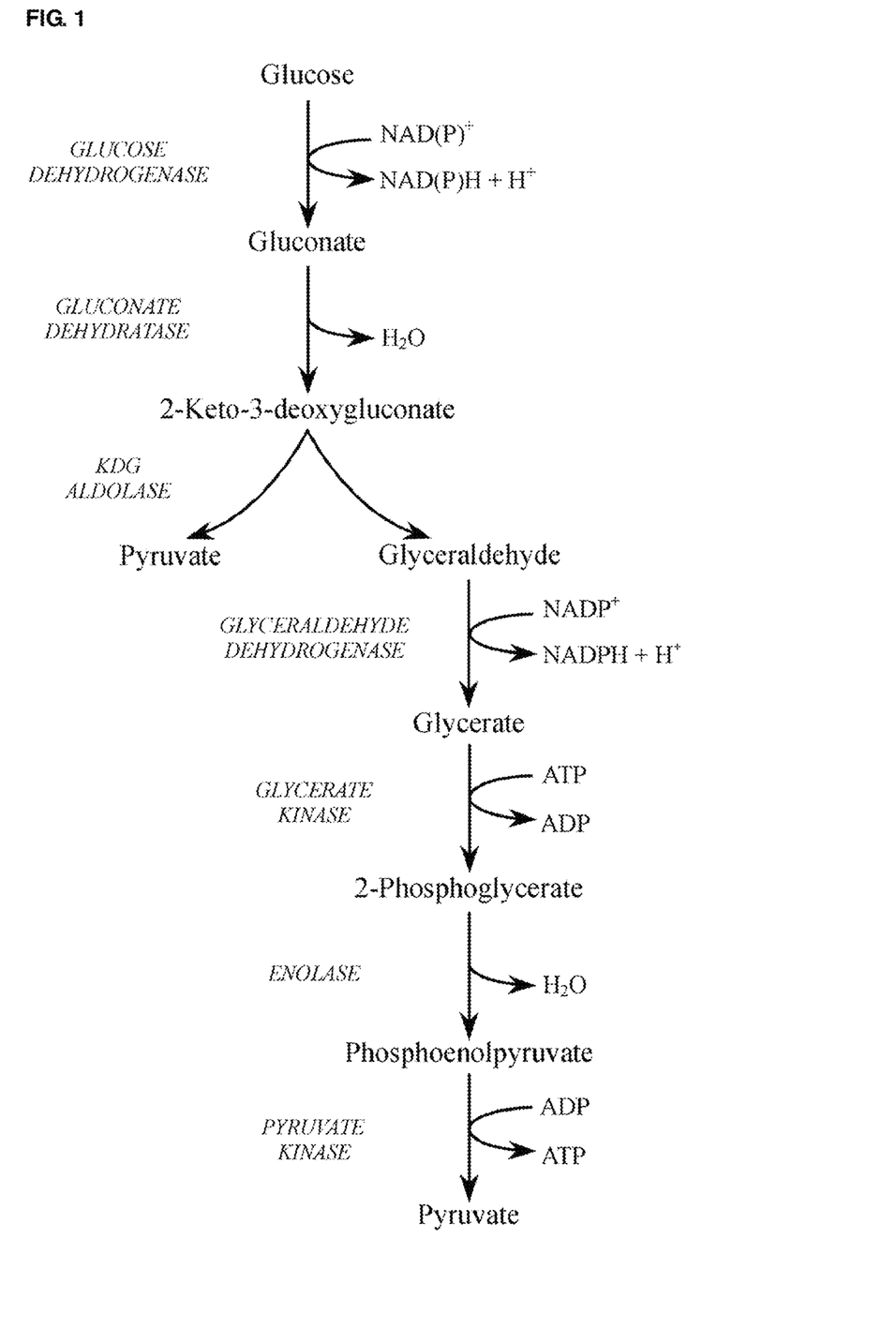
FIG. 1 is a non-phosphorylated ED pathway.

In many hyperthermophilic archaea habited in these biotops, the order Sulfolobales which includes the genus *Sulfolobus*, have a chemolithoautotrophic metabolism which converts elemental sulfur to hydrogen sulfide using organic compounds or hydrogen as an electron donor. Although *Sulfolobus* is the sulfur-oxidizing genus, this genus can grow chemoheterotrophically to a high cell density using sugars. *Sulfolobus solfataricus* optimally grows at 80-85° C. and pH 2-4, utilizing glucose as the sole carbon and energy source (Grogan, *J. Bacteriol.* 171:6710-6719, 1989)). In *Sulfolobus*, the glucose metabolism pathway was first analyzed with $^{14}$C-glucose-label experiments by De Rosa et al. (*Biochem. J.* 224: 407-414, 1984). De Rosa's experiment shows that *Sulfolobus* can convert glucose to pyruvate through a modified Entner-Doudoroff (ED) pathway which produces non-phosphorylated intermediates such as gluconate, 2-keto-3-deoxygluconate (KDG), and glyceraldehyde. The first reaction of the non-phosphorylated ED pathway in *S. solfataricus* involves the NAD(P)$^+$-dependent oxidation of glucose to gluconate, catalyzed by glucose dehydrogenase. Gluconate is then dehydrated by gluconate dehydratase (EC 4.2.1.39) to 2-keto-3-deoxygluconate (KDG), which is cleaved to pyruvate and glyceraldehydes, and catalyzed by KDG-alolase (EC 4.1.2.20). The modified ED pathway involving non-phosphorylated intermediates was also discovered in thermoacidophilic archaeon *Thermoplasma acidophilum* (Budgen et al. *FEBS Lett.* 196:207-210, 1986). The *Thermoplasma acidophilum* metabolizes glyceraldehyde formed via this non-phosphorylated route by glyceraldehyde dehydrogenase to glycerate, which is phosphorylated to form 2-phosphoglycerate. This intermediate is then converted to generate one molecule of pyruvate by enolase and pyruvate kinase. The non-phosphorylated ED pathway is a unique glycolysis pathway discovered only in the thermoacidophilic archaea, *S. solfataricus* and *T. acidophilum*. FIG. 1 is a non-phosphorylated ED pathway.

Another modified ED pathway involving phosphorylated intermediates is known as a novel glycolysis route for glucose conversion to pyruvate in some species. This metabolism was first discovered by Szymona et al. from eubacteria *Rhodobacter sphaeroides*, and was also later found from *Clostridia* sp. and halobacteria (Conway, *FEMS Microbiol. Rev.* 103:1-28, 1992). In this pathway, KDG produced by gluconate dehydratase is phosphorylated by KDG kinase to 2-keto-3-deoxy-6-phosphogluconate (KDPG) and is then cleaved by KDPG aldolase to pyruvate and glyceraldehyde-3-phosphate. The latter intermediate is oxidized to pyruvate, a process that involves a conventional route, via glyceraldehyde-3-phosphate dehydrogenase, phosphoglycerate mutase, enolase, and pyruvate kinase.

Gluconate dehydratase has described by Kersters et al., *Antonie van Leeuwenhoek.* 37: 233-246 (1971); Kersters et al., *Methods Enzymol.* 42: 301-304 (1975); Bender et al., *Eur. J. Biochem.* 40: 309-321 (1973); Bender et al., *Methods Enzymol.* 90: 283-287 (1982). The protein was purified and characterized only from bacteria, *Achromobacter* species, and *Clostridium pasteurianum*, which metabolize gluconate via a former glycolysis pathway. A comparison of the biochemical properties of each enzymes shows that they are very different despite in vivo the same catalytic reaction. In thermoacidophilic archaea, *S. solfataricus*, and *T. acidophilum*, however biochemical properties and detail mechanisms of the gluconate dehydratases are still unknown. Despite characterizations of two enzymes from the above-described bacteria, no genes encoding gluconate dehydratase or partial amino acid sequences have been reported. Hence, although recently the genomes of *S. solfataricus* and *T. acidophilum* were completely sequenced, putative genes encoding gluconate dehydratase could not be annotated in the database (She et al., *Proc. Natl. Acad. Sci. USA.* 98: 7835-7840, 2001; Ruepp et al., *Nature* 407:508-513, 2000). In addition, the known gluconate dehydratases do not maintain thermostability at temperatures greater than about 50° C. for prolonged periods up to several hours. Thus it is necessary to develop a novel gluconate dehydratase that can retain activity at high temperatures for prolonged periods of time.

DISCLOSURE OF INVENTION

Technical Problem

To solve the problems of the prior art, it is an aspect of the present invention to provide a novel thermostable gluconate dehydratase isolated from thermoacidophilic archaea species.

It is another aspect of the present invention to provide an amino acid sequence of protein having gluconate dehydratase activity.

It is another aspect of the present invention to provide a nucleic acid sequence encoding a gluconate dehydratase.

It is another aspect of the present invention to provide a biological expression system of a gluconate dehydratase and a transformant expressing the gluconate dehydratase.

It is another aspect of the present invention to provide an in vitro method of conversion aldonic acid into 2-keto-3-deoxy aldonic acid.

Technical Solution

In order to accomplish the aspects of the present invention, the present invention provides a polynucleotide encoding a gluconate dehydratase, wherein the gluconate dehydratase comprises a polynucleotide having at least a 50% identity to a nucleic acid sequence encoding an polypeptide comprising amino acid sequences of SEQ ID NO:2 or a polynucleotide complementary to the polynucleotide having at least a 50% identity to a polynucleotide encoding an polypeptide comprising amino acid sequences of SEQ ID NO:2

The present invention provides a polypeptide comprising an amino acid sequence which is at least 50% identical to an amino acid sequence of SEQ ID NO:2, wherein the polypeptide catalyzes dehydration of aldonic acid to 2-Keto-3-deoxy aldonic acid.

The present invention provides an expression construct comprising a polynucleotide comprising a nucleic acid sequence having at least a 50% identity to a nucleotide sequence encoding an polypeptide comprising an amino acid sequence of SEQ ID NO:2 or a polynucleotide complementary to a polynucleotide comprising a nucleic acid sequence having at least a 50% identity to a nucleotide sequence encoding a polypeptide comprising an amino acid sequence of SEQ ID NO: 2, wherein the polynucleotide is operably linked to and under the regulatory control of a transcription and translation regulatory sequence.

The present invention provides an organism transformed with a vector comprising a polynucleotide encoding gluconate dehydratase, operably linked to and under the regulatory control of a transcription and translation regulatory sequence.

The present invention provides a method for preparing a protein, comprising:

(a) preparing a vector comprising a polynucleotide encoding gluconate dehydratase, operably linked to and under the regulatory control of a transcription and translation regulatory sequence;

(b) introducing the vector into a host cell and selecting a transformant expressing the protein;

(c) culturing the transformant under a condition which permits the protein to be expressed; and (d) purifying the protein from intracellular material of the transformant, and wherein the protein catalyzes a dehydration of aldonic acid to 2-keto-3-deoxy aldonic acid.

The present invention provides a method of preparing an organism expressing a protein, comprising:

(a) preparing a vector comprising a polynucleotide encoding gluconate dehydratase, operably linked to and under the regulatory control of a transcription and translation regulatory sequence;

(b) introducing the vector into a host cell; and (c) selecting a transformant expressing the protein, and wherein the protein catalyzes dehydration of aldonic acid to 2-keto-3-deoxy aldonic acid.

The present invention provides a method of purifying gluconate dehydratase, comprising:

(a) harvesting a cell from the culture solution of gluconate dehydratase producing microorganism;

(b) obtaining a supernatant from intracellular material of the cell;

(c) conducting chromatography of the supernatant through a column packed with DEAE-Sepharose to collect an eluant;

(d) conducting chromatography of the eluant of step (c) through a column packed with Q-Sepharose to collect an eluant;

(e) conducting chromatography of the eluant of step (d) through a column packed with Phenyl-Sepharose to collect an eluant; and (e) conducting chromatography of the eluant of step (e) through a Mono Q HR 5/5 column to collect a fraction.

The present invention provides a method for producing a 2-keto-3-deoxy aldonic acid from aldonic acid, comprising contacting the gluconate dehydratase to aldonic acid in water or an aqueous solvent at temperatures from 0° C. to 120° C. and pH 1.5 to 12, wherein the blend ratio of gluconate dehydratase to aldonic acid is 1 ug:0.01 to 1 mol.

DESCRIPTION OF DRAWINGS

A more complete appreciation of the invention, and many of the attendant advantages thereof, will be readily apparent as the same becomes better understood by reference to the following detailed description when considered in conjunction with the accompanying drawings, wherein.

MODE FOR INVENTION

In the following detailed description, only selected embodiments of the invention have been shown and described, simply by way of illustration of the best mode contemplated by the inventors of carrying out the invention. As will be realized, the invention may be modified in various respects, all without departing from the invention. Accordingly, the drawings and description are to be regarded as illustrative in nature, and not restrictive.

As used herein, 'purified' or 'isolated' refer to a nucleic acid or polypeptide that is substantially free of cellular or viral material with which it is naturally associated, a culture medium (when produced by recombinant DNA techniques), chemical precursors, or other chemicals (when chemically synthesized). Moreover, an isolated nucleic acid fragment is a nucleic acid fragment that is not naturally occurring as a fragment and would not be found in the natural state.

As used herein, 'nucleic acid or polynucleotide' include both RNA and DNA, including genomic DNA, cDNA, and synthetic (e.g., chemically synthesized) DNA. Nucleic acid can be double-stranded or single-stranded. Where single-stranded, the nucleic acid or polynucleotide can be a sense strand or an antisense strand. The nucleic acid or polynucleotide can be synthesized using oligonucleotide analogs or derivatives (e.g., inosine or phosphorothioate nucleotides).

As used herein, 'thermostable', when referring to an enzyme, means an enzyme which can function and is stable at high temperatures, is heat resistant, and will not denature at high temperatures.

A. Thermostable Gluconate Dehydratase

As used herein, the term 'thermostable gluconate dehydratase' in the context of the present invention refers to an enzyme which:

(1) is thermostable, i.e. substantially retains enzymatic activity upon exposure to heat at a temperature above 60-120° C., preferably above 80° C., and more preferably above 90° C.; and (2) catalyzes aldonic acid to 2-keto-3-deoxy aldonic acid, and moreover preferably reacts gluconic acid to 2-keto-3-deoxy gluconic acid.

A gluconate dehydratase of the present invention can be isolated or purified from the thermoacidophilic archaea species, preferably microorganisms belong to *Sulfolobus* genus, and more preferably *Sulfolobus solfataricus, Sulfolobus acidocaldarius, Sulfolobus shibatae, Sulfolobus tokodaii, Sulfolobus metallicus, Sulfolobus hakonensis, Sulfolobus brierleyi, Sulfolobus islandicus, Sulfolobus tengchongensis, Sulfolobus thuringiensis, Sulfolobus yangmingensis, Sulfolobus* sp., *Thermoplasma acidophilum, Thermoplasma volcanium, Ferroplasma acidophilum,* or *Sulfolobus* strains AMP12/99, CH7/99, FF5/00, MV2/99, MVSoil3/SC2, NGB23/00, NGB6/00, NL8/00, NOB8H2, RC3, RC6/00, and RCS1/01.

The gluconate dehydratase of the present invention is thermostable and maintains catalytic activity after a treatment of about 80° C. to about 90° C. for 30 minutes. The thermostable range is from 0° C. to 120° C., preferably from 20° C. to 100° C., and more preferably from 30° C. to 90° C., and the optimum temperature is about 85° C. The gluconate dehydratase keeps its activity in a pH range of 1.5 to 12, preferably from 1.5 to 10, more preferably from 4.0 to 9.0, and most preferably from 6 to 8, affording a wide range of hybridization conditions in which the enzyme is active.

The aldonic acid as substrate for gluconate dehydratase may include D-gluconate, D-Galactonate, D-Galactoheptonate, D-Arabonate, D-glucuronate, L-gulonate, D-tartarate, D-glucarate, L-isovalerate, L-threonate, D-ribonate, L-tartarate, D-gulonate, and D-galactarate but is not limited to. The embodiment of the present invention includes a D-gluconate as the preferred substrate for gluconate dehydratase derived from *S. solfataricus*.

The gluconate dehydratase of the present invention includes a polypeptide with biological activity that is at least about 50%, 60%, 70%, 75%, 80%, 85%, 90%, 95%, 96%, 97%, 98%, or 99% identical to the amino acid sequence represented by SEQ ID NO:2. The nucleic acid sequence of the gluconate dehydratase includes a polynucleotide encoding polypeptide that has at least about 50%, 60%, 70%, 75%, 80%, 85%, 90%, 95%, 96%, 97%, 98%, or 99% identical to the polypeptide sequence represented by SEQ ID NO:2 or its complements. The preferable nucleic acid sequence include a polynucleotide that is at least about 70%, 75%, 80%, 85%, 90%, 95%, 96%, 97%, 98%, or 99% identical to of SEQ ID NO:1 or its complements. The nucleic acid sequence can further contain an immediately contiguous sequence with both of the coding sequences (one on the S end and one on the 3' end).

In one embodiment, the gluconate dehydratase from *S. solfataricus* (Ss) that is designated herein as Ss gluconate dehydratase was isolated and characterized. The Ss gluconate dehydratase has about 320,000 to 380,000 daltons as a native form, and has about 40,000 to 50,000 daltons as determined by SDS-PAGE under denaturing (reducing) conditions. These results indicate that the *S. solfataricus* gluconate dehydratase in its native conformation is an octamer consisting of eight identical subunits. The sequence of gene coding by the Ss gluconate dehydratase includes the nucleotide sequence of SEQ ID NO:1.

B. Isolation and Purification of Thermostable Gluconate Dehydratase

The gluconate dehydratase can be isolated and purified from thermoacidophilic archaea species, or chemically or biochemically synthesized by expression in a prokaryotic or eukaryotic host (for example, by bacterial, yeast, higher plants, insects, and mammalian cells in culture).

The purification of gluconate dehydratase can be carried out by methods well known to those skilled in the art, i.e., chromatography. The chromatography can be conducted with the common resin attached thereto, with one or more kinds of functional groups selected from the group consisting of carboxy, carboxymethyl, sulpho, sulphomethyl, sulphoprophyl, aminoethyl, diethylaminoethyl, trimethylaminomethyl, triethylaminoethyl, dimethyl-2-hydroxyethylaminomethyl, diethyl-2-hydroxypropylaminoethyl, phospho, alkyl (ex, hexyl-, octyl-, phenyl-) and hydroxylapatite. The matrix of the resin can be selected from the group consisting of agarose, cellulose, dextran, polyacrylate, and polystyrene.

In one embodiment, the present invention provides a purification method of gluconate dehydratase. The isolation and purification of gluconate dehydratase is performed at below room temperature to room temperature, preferably at about 4° C.

In the first step, the cells expressing the gluconate dehydratase are harvested, typically by centrifugation or filtration. In the steps, all buffers contain a stabilizing agent or the like to increase the activity and yield of a gluconate dehydratase preparation.

In the second step, the cells are lysed and the supernatant is segregated and recovered from cellular debris. Lysis is typically accomplished by mechanically applying physical stress and/or enzymatic digestion, and segregation of the supernatant is usually accomplished by centrifugation.

In the third step, the supernatant is further purified by chromatography with a weak anionic exchange column. In the embodiment, the supernatant from the second step is applied to DEAE-Sepharose from Pharmacia (Piscataway, N.J., USA) equilibrated with a column buffer (50 mM trihydroxymethylaminomethane (Tris), pH 7.2). The column is washed with a column buffer to remove unwanted macromolecules, and the bound protein is then eluted off the column with the column buffer in a linear gradient of 0-1.0 molar (M) NaCl. In the case of Ss gluconate dehydratase, it is eluted at about 0.5 M NaCl. The eluant fractions are collected and centrifuged to remove any insoluble material. The collected eluant is segregated, usually dialyzed, and then recovered to form a fraction containing partially purified gluconate dehydratase.

In the fourth step, the fraction containing gluconate dehydratase is further purified by chromatography with a strong anionic exchange column. In the embodiment, the fraction is applied to Q-Sepharose from Pharmacia (Piscataway, N.J., USA) equilibrated with a column buffer (50 mM trihydroxymethylaminomethane (Tris), pH 7.2). The column is washed with the column buffer to remove unwanted macromolecules, and the bound protein is then eluted off the column with the column buffer in a linear gradient of 0-1.0 molar (M) NaCl. In the case of Ss gluconate dehydratase, it is eluted at about 0.5 M NaCl. The eluant fractions are collected and centrifuged to remove any insoluble material. The collected eluant is segregated, usually dialyzed, and then recovered to form a fraction containing partially purified Ss gluconate dehydratase.

For increasing purity of the gluconate dehydratase, the fraction prepared by the fourth step can be applied to a Phenyl-Sepharose column equilibrated with 50 mM Tris-HCl, pH 7.2 containing 1.0 M NaCl. After washing with the same buffer, the enzyme is eluted by a decreasing salt gradient of 1.0 to 0.0 M NaCl. Active fractions, collected at a flow rate of 0.5 ml/min, are pooled, concentrated by ultrafiltration, and loaded on a Mono Q HR 5/5 column equilibrated with 50 mM Tris-HCl, pH 7.2. The enzyme is eluted with linear gradient of 0.0-1.0 M NaCl. Active fractions are collected, pooled, concentrated with an ultrafiltration membrane, and desalted with HiTrap™ desalting (Pharmacia, Sweden) to eliminate remaining NaCl in enzyme fractions.

C. Identification of the Isolated and Purified Gluconate Dehydratase and Gene Thereof The amino acid sequence of the isolated or/and purified gluconate dehydratase can be partially or fully determined by a method well known in the art, such as by automated Edman degradation, and the like. The determined amino acid sequence can be used for screening a novel protein having homology in a database or/and for deducing coding nucleic acids. Then, a novel gene encoding gluconate dehydratase from various organisms can be screened through a suitable method such as PCR, sequencing, and so on.

The target organism may be an archaea species including *Sulfolobus solfataricus, Sulfolobus acidocaldarius, Sulfolobus shibatae, Sulfolobus tokodaii, Sulfolobus metallicus, Sulfolobus hakonensis, Sulfolobus brierleyi, Sulfolobus islandicus, Sulfolobus tengchongensis, Sulfolobus thuringiensis, Sulfolobus yangmingensis, Sulfolobus* sp., *Thermoplasma acidophilum, Thermoplasma volcanium, Ferroplasma acidophilum,* and *Sulfolobus* strains AMP12/99, CH7/99, FF5/00, MV2/99, MVSoil3/SC2, NGB23/00, NGB6/00, NL8/00, NOB8H2, RC3, RC6/00, and RCS1/01.

In one embodiment of the present invention, portions of the genomic DNA encoding at least six contiguous amino acids are synthesized and used as probes to clone full-length genes of gluconate dehydratase. The nucleic acid encoding Ss gluconate dehydratase and a flanked sequence thereto are identified. The open reading frame for Ss gluconate dehydratase is shown in SEQ ID NO:1, and the nucleic acid sequence including the 3' and 5-flanked sequences is shown in SEQ ID NO:5.

Also, because there may not be a precisely exact match between the nucleotide sequence in the *S. solfataricus* as described herein and that in the corresponding portion of the other species or strain, oligomers containing approximately 18 nucleotides (encoding the six amino acid stretch) may be necessary to obtain hybridization under conditions of sufficient stringency to eliminate false positives.

Alternatively, polyclonal antiserum from rabbits immunized with purified Ss gluconate dehydratase of the present invention can be used to probe a *S. solfataricus* partial genomic expression library to obtain the appropriate coding sequence.

D. Expression System of Thermostable Gluconate Dehydratase

A gluconate dehydratase can also be produced by recombinant DNA (rDNA) techniques. The gene encoding a thermostable gluconate dehydratase can be operably linked to an expression system to form an rDNA capable of expression in a compatible host. Exemplary vectors and expression are described herein.

The gene encoding a thermostable gluconate dehydratase includes a wild type DNA or DNA altered by modification, substitution, deletion, or addition of nucleic acid without substantially altering its catalytic activity or thermostability, and such changes in sequence is acceptable and preferable where such changes impart desirable characteristics upon the enzyme.

(1) Construction for Expression of Gluconate Dehydratase

For expression of the gluconate dehydratase, an expression construct including a polynucleotide encoding gluconate dehydratase, wherein the polynucleotide is operably linked to and under the regulatory control of a transcriptional and translational regulatory sequence, can be prepared. The transcriptional and translational regulatory sequences are those which can function in a specific organism (i.e., bacteria, yeast, fungi, plants, insects, animals, and humans) cell or tissue to effect the transcriptional and translational expression of the foreign gene with which they are associated and can be employed according to host cell. The examples of transcriptional and translational regulatory sequences include a promoter, enhancer, polyadenylation signal, and terminator, but are not limited thereto.

The promoter can be derived from a highly-expressed gene to direct transcription of a downstream structural sequence. Such promoters can be derived from operon encoding glycolytic enzymes such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions can be employed, and examples are alcohol dehydrogenase 2, isocytochrome C, α-factor, acid phosphatase, heat shock proteins, degradative enzymes associated with nitrogen metabolism, and enzymes responsible for maltose or galactose utilization. And the promoter may be the known promoter contained in the common vectors lacI, lacZ, T3, T7, lamda $P_R$, $P_L$, trp, CMV immediate early, HSV thymidine kinase, early and late SV40, LTRs from retroviruses, and mouse metallothionein-I. Selection of the appropriate promoter is well within the level of ordinary skill in the art.

The enhancer is a cis-acting elements of DNA, usually from about 10 to 1000 bp that act on a promoter to increase its transcription. Examples include the SV40 enhancer on the last side of the replication origin by 100 to 270, a cytomegalovirus early promoter enhancer, the late side of the replication origin, and adenovirus enhancers.

The expression construct can further include a multi-cloning site, selectable marker, origins of replication and selectable markers permitting transformation of the host cell, e.g., the ampicillin resistance gene and N-terminal identification peptide imparting desired characteristics, e.g., a sequence for stabilizing or a simplified purification process of expressed recombinant protein, a ribosome binding site, or/and report gene. The expression construct may be a common vector, and examples are a plasmid or viral vector. Large numbers of suitable vectors are known to those of skill in the art, and are commercially available. The following vectors are provided by way of example: pRSET, pTrcHis, pBAD, pTOPO, pTrx-Fus, pThioHis (Invitrogen), pET-19, 21, 24, 32, 43 (Novagen), pQE-30, -31, -32, pQE-40, -41, -42, pQE-50, -51, -52, pQE-16, -17, -18, pQE-60, pQE-70, pQE-9, -10, -11 (Qiagen), pBluscript II (Stratagene), pTrc99a, pKK223-3, pDR540, pRIT2T (Amersham-Pharmacia), pXT1, pSG5 (Stratagene); pSVK3, pBPV, pMSG, pSVLS40 (Amersham-Pharmacia), pBR322 (ATCC37017); pKK223-3 (Amersham-Pharmacia, Sweden), and pGEM1 (Promega, USA). However, any other plasmid or vector may be used as long as they are replicable and viable in the host.

The suitable host for producing a recombinant protein includes a eukaryote, a prokaryote or virus. The eukaryote can be selected from the group consisting of a yeast, insect, animal, plant, and human, and a cell derived therefrom, and the prokaryote can be a microorganism including *E. coli, Streptomyces, Bacillus subtilis,* and fungi. Examples of the insect cell are *Drosophila* S2 and *Spodoptera* Sf9, Examples of mammalian expression systems include the COS-7 lines of monkey kidney fibroblasts, described by Gluzman (Cell, 23:175, 1981), and other cell lines capable of expressing a compatible vector, for example, the C127, 3T3, CHO, HeLa, and BHK cell lines.

(2) Establishment of Transformant

Techniques for generating transformants according to host cell type are well known, for example calcium phosphate transfection, DEAE-Dextran mediated transfection, electrophoration (Davis, L., Dibner, M, Battey, I., *Basic Methods in Molecular Biology*, 1986), and *Agrobacterium tumefaciens*-mediated DNA transfer.

In one embodiment of the present invention, pGNH vectors harboring Ss gluconate dehydratase genes were prepared to be introduced into *Escherichia coli* BL21(DE3) following select transformants. The transformants are designed as *Escherichia coli* BL21(DE3)/pGNH and been deposited pursuant to Budapest Treaty requirements with the Korean Collection for Type Cultures (KCTC), Taejon, Republic of Korea, in Apr. 9, 2004, and were assigned accession number KCTC 10619BP.

Figure 2:
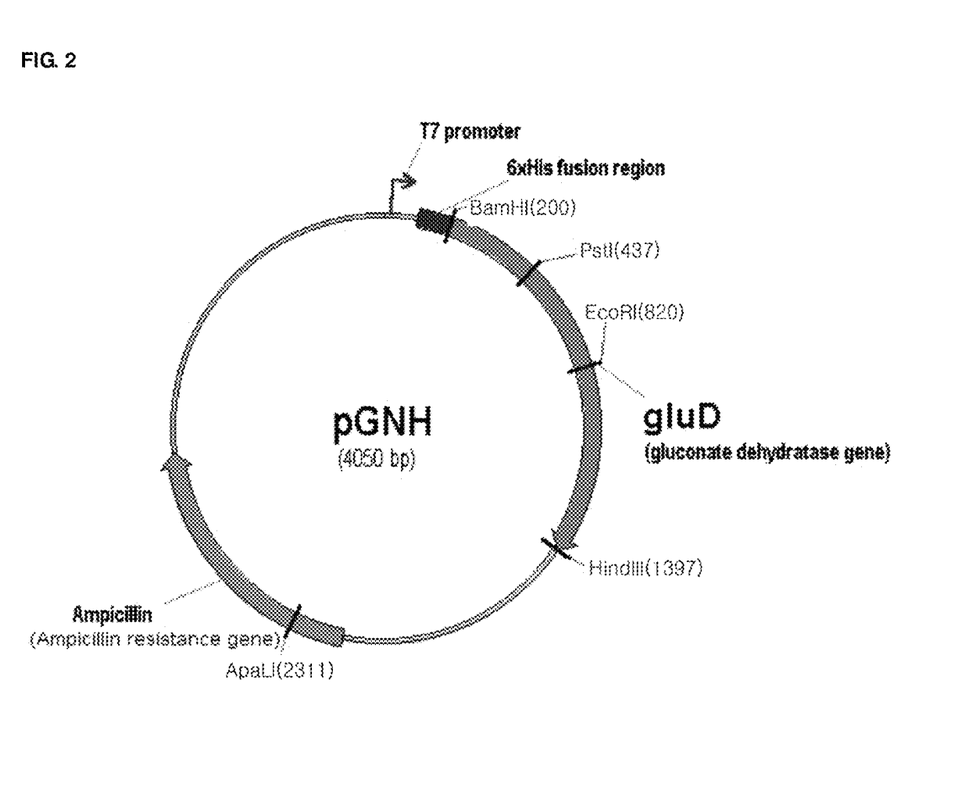
FIG. 2 is a vector map of pGNH.

The pGNH vector includes a Ss gluconate dehydratase coding portion and control sequences at the 5 and 3' termini of the coding portion on between BamHI and HindIII restriction sites. The sequence of pGNH is shown in SEQ ID NO:3, and loci of each component are represented in Table 1 and FIG. 2.

TABLE 1

| pGNH vector | | |
| --- | --- | --- |
| Component | Name | loci |
| Promoter | T7 promoter | 20-39 |
| Foreign gene | gluD (gluconate dehydrates coding gene) | 208-1396 |
| Selection marker | Ap (ampicillin resistance gene) | 2149-2963 |
| His-tag fusion region | 6xHis fusion region | 100-207 |

(3) Production of the Recombinant Gluconate Dehydratase

Transformants are cultured in a condition for expressing the recombinant gluconate dehydratase according to the known method. The cultured cells employed in expression of proteins can be disrupted by any convenient method, including freeze-thaw cycling, sonication, mechanical disruption, or use of cell lysing agents, and such methods are well known to those skilled in the art. Cell are typically harvested by centrifugation, disrupted by physical or chemical means, and the resulting crude extract retained for further purification.

In case of *Escherichia coli* BL21(DE3)/pGNH, a preferable culture condition for expressing the recombinant Ss gluconate dehydratase includes follows:

Medium: Luria-bertani medium, M9 medium, SOB (SOC) medium, Terrific Broth
Temperature: 20-40° C.
Culture time: 6-42 hrs (4) Recover of Recombinant Protein The recombinant gluconate dehydratase can be recovered and purified from recombinant cell cultures by any convenient method including ammonium sulfate precipitation, acetone precipitation, acid extraction, anion exchange chromatography, cation exchange chromatography, hydrophobic interaction chromatography, phosphocellulose chromatography, affinity chromatography, hydroxylapatite chromatography, and lectin chromatography, and preferably by a method of the present invention mentioned above. Protein refolding steps can be used, as necessary, in completing configuration of the mature protein. Finally, high performance liquid chromatography (HPLC) can be employed for final purification steps.

Depending upon the host employed in a recombinant production procedure, the recombinant Ss gluconate dehydratase of the present invention may or may not be a post-translational modification, such as through glycosylation, phosphorylation, and acetylation. Enzymes of the invention also may or may not include an initial methionine amino acid residue.

In an embodiment of the present invention, recombinant Ss gluconate dehydratase from *Escherichia coli* BL21(DE3)/pGNH is purified by nickel affinity chromatography.

E. Use of Gluconate Dehydratase

The gluconate dehydratase may be employed for any purpose in which such enzyme activity is necessary or desired. In a preferred embodiment the enzyme is employed for catalyzing the dehydration of aldonic acid. The dehydration of aldonic acid may be used for the production of carbohydrate intermediates used in pharmaceutical, agricultural, and other chemical products.

The gluconate dehydratase, their fragments, derivatives, or analogues thereof, or recombinant gluconate dehydratase, can be used as an immunogen to produce antibodies thereto. These antibodies can be, for example, polyclonal or monoclonal antibodies. The present invention also includes chimeric, single chain, and humanized antibodies, as well as Fab fragments, and the product of a Fab expression library. Various procedures known in the art may be used for the production of such antibodies and fragments.

Antibodies generated against the gluconate dehydratase can be obtained by direct injection of the enzymes into an animal or by administering the enzymes to an animal, preferably a nonhuman. The antibody obtained then binds the gluconate dehydratase itself. In this manner, even a sequence encoding only a fragment of the gluconate dehydratase can used to generate antibodies and can then be used to isolate the enzyme from cells expressing that gluconate dehydratase.

For preparation of monoclonal antibodies, any technique which provides antibodies produced by continuous cell line cultures can be used. Examples include the hybridoma technique (Kohler and Milstein, Nature, 256:495-497, 1975), the trioma technique, the human B-cell hybridoma technique (Kozbor et al., Immunology Today, 4:72, 1983), and the EBV-hybridoma technique to produce human monoclonal antibodies (Cole et al., In *Monoclonal Antibodies and Cancer Therapy*, Alan R. Liss, Inc., pp 77-96, 1985).

Techniques described for the production of single chain antibodies (U.S. Pat. No. 4,946,778) can be adapted to produce single chain antibodies for immunogenic enzyme products of the present invention. Also, transgenic mice may be used to express humanized antibodies to immunogenic enzyme products of this invention.

Antibodies generated against the gluconate dehydratase of the present invention may be used in screening for similar enzymes from other organisms and samples. Antibodies may also be employed as a probe to screen gene libraries generated from this or other organisms to identify this or cross reactive activities.

F. Production of 2-keto-3-deoxy Aldonic Acids from Aldonic Acids

The gluconate dehydratase dehydrates aldonic acid to 2-keto-3-deoxy aldonic acid. Thus the gluconate dehydratase of the present invention can be used for production 2-keto-3-deoxy aldonic acid from aldonic acid.

The present invention provides a method of producing 2-keto-3-deoxy aldonic acid from aldonic acid including contacting the gluconate dehydratase to aldonic acid in water or an aqueous solvent at temperatures from 0° C. to 120° C. and pH 1.5 to 12, wherein the blend ratio of gluconate dehydratase to aldonic acid is 1 ug:0.01 to 1 mol.

The gluconate dehydratase can be selected from the group consisting of an isolated native gluconate dehydratase, a chemically synthesized gluconate dehydratase, a recombinant gluconate dehydratase, and derivatives thereto.

The aldonic acid prefers D-gluconate, D-Galactonate, D-Galactoheptonate, D-Arabonate, D-glucuronate, L-gulonate, D-tartarate, D-glucarate, L-isovalerate, L-threonate, D-ribonate, L-tartarate, D-gluconate, and D-galactarate.

The dehydration reaction of aldonic acid is conveniently carried out at temperatures from 0° C. to 120° C., preferably from 20° C. to 100° C., and most preferably from 30° C. to 90° C.

The suitable pH for effecting the enzyme reaction is from 1.5 to 12, preferably from 1.5 to 10, and most preferably from 4.0 to 9.0.

The concentration of the substrate and aldonic acids in the reaction mixture is conveniently from 1 to 700 g/L, preferably from 10 to 500 g/L, and most preferably from 50 to 200 g/L.

The optimum condition for the dehydration reaction of aldonic acid includes the gluconate dehydratase concentration of 0.1-1 mg/mL, substrate concentration of 100-200 mM, reaction time of less than 6 hr, temperature of 70-95° C., and pH of 7.0-8.0.

The reaction is conveniently carried out in water or an organic solvent. The organic solvent is selected from the group consisting of alcohol, 0.01 to 100% of aqueous alcohol, and a mixture of several alcohols, aromatic hydrocarbon, and aliphatic hydrocarbon. The alcohol is preferably a $C_{1-6}$-alkanol, such as methanol, ethanol, n-propanol, isopropanol, n-butanol, isobutanol, or tert-butanol. The aliphatic hydrocarbon alcohol is preferably heptane or isooctane, and the aromatic hydrocarbon alcohol is preferably benzene or toluene. From an economic and environmental point of view, as little organic solvent as possible is used in the industrial process.

The dehydration reaction can be carried out in a condition of addition of an antioxidant, such as 2-mercaptoethanol, dithiothreitol, or cysteine, to prevent the degradation of the produced 2-keto-3-deoxy acid analogues.

As an alternative to a gluconate dehydratase itself, the reaction mixture may comprise an organism having gluconate dehydratase activity.

For the reaction, any form of the gluconate dehydratase enzyme can be used, in particular an enzyme solution, the immobilized enzyme, intact cells of the organism having gluconate dehydratase activity, and immobilized cells having gluconate dehydratase activity.

The following examples are provided to further illustrate the present invention and are not intended to limit the invention beyond the limitations set in the appended claims.

Example 1

Cultivating *Sulfolobus solfataricus* and Preparing Ss Cell Paste

The following describes how the hyperthermophilic archaeon *S. solfataricus* is routinely grown in a 3.7 liter fermentor for the purpose of obtaining cell mass in sufficient quantities for large scale protein purification.

For culture maintenance, *S. solfataricus* P2 (DSM1617) is routinely grown at 75-85° C. as a closed shaking culture at a volume of 100 ml. The organism was cultivated in the medium (per liter, 3.0 g glucose, 3.0 g yeast extract, 1.3 g $(NH_4)_2SO_4$, 0.28 g $KH_2PO_4$, 0.25 g $MgSO_4.7H_2O$, 0.07 g $CaCl_2.H_2O$) containing 1 ml trace metal solution (20 mg $FeCl_3.H_2O$, 4.5 mg $Na_2B_4O_7.H_2O$, 1.8 mg $MnCl_2.H_2O$, 0.05 mg $ZnSO_4.H_2O$, 0.05 mg $CuCl_2.H_2O$, 0.04 mg $VOSO_4.H_2O$, 0.03 mg $Na_2MoO_4.H_2O$, 0.01 mg $CoSO_4.H_2O$ per liter). The final pH was adjusted to pH 3.0 with 1 M $H_2SO_4$. Cultures were grown aerobically in a 3.7-liter fermentor (KLF 2000, Bioengineering AG, Switzerland) at 78° C. while being stirred at 400 rpm. Growth was monitored spectrophotometrically at 540 nm.

Example 2

Purification of Gluconate Dehydratase from *Sulfolobus solfataricus*

Cells of *S. solfataricus* (frozen wet cell weight 35 g) were harvested by centrifugal ion (5000×g, 30 min, 4° C.) and washed twice with 50 mM Tris-HCl (pH 7.2). Cell pellets were re-suspended in 50 mM Tris-HCl (pH 7.2), and disrupted by sonication for 1 h at 50% output. Crude extracts were heated at 90° C. for 20 min., and heat-denatured proteins and cell debris were removed by centrifugation (50000×g, 1 h, 4° C.). To the supernatant solution was added solid $(NH_4)_2SO_4$ up to 40% saturation to recover a fraction containing the activity of gluconate dehydratase. After centrifugation (50000×g, 1 h, 4° C.), the soluble fraction was dialyzed in 50 mM Tris-HCl (pH 7.2). The homogenate was loaded onto a DEAE-Sepharose column (2.5×16 cm) previously equilibrated with 50 mM Tris-HCl, pH 7.2, and the elution was performed with a three bed volume of the same buffer, followed by a linear gradient of 0.0-1.0 M NaCl. Fractions (5 ml each) were collected at a flow rate of 1 ml/min. Those with gluconate dehydratase activity were pooled, concentrated by ultrafiltration on a Vivaspin™ concentrator membrane (Vivascience, Lincoln, UK) and loaded on a Phenyl-Sepharose column (1.0×10 cm) equilibrated with 50 mM Tris-HCl, pH 7.2, containing 1.0 M NaCl. After washing with the same buffer, the enzyme was eluted by a decreasing salt gradient of 1.0 to 0.0 M NaCl. Active fractions, collected at a flow rate of 0.5 ml/min, were pooled, concentrated by ultrafiltration, and loaded on a Mono Q HR 5/5 column (0.5×5 cm) equilibrated with 50 mM Tris-HCl, pH 7.2. The enzyme was eluted with a linear gradient of 0.0-1.0 M NaCl. Active fractions, collected at a flow rate of 0.5 ml/min, were pooled, concentrated with ultrafiltration membrane, and desalted with HiTrap™ desalting (Pharmacia, Sweden) to eliminate remaining NaCl in enzyme fractions.

The resulting product is referred to as Ss gluconate dehydratase. The resultant Ss gluconate dehydratase was determined to be 95% homogeneous by analysis of SDS-polyacrylamide gel electrophoresis (SDS-PAGE)

Example 3

Assay of the Gluconate Dehydratase

Ss Gluconate dehydratase activity was measured by the semicarbazide method or TBA (thiobarbituric acid) assay.

The semicarbazide method was performed as follows: an enzyme reaction of a total volume a 400 µl was incubated at 78° C. in 50 mM Tris-HCl buffer, pH 7.0, with 10 mM gluconate and an enzyme solution. After 30 min, the enzyme reaction was stopped by the addition of 100 µl 2.0 M HCl. To this solution, 300 µl of semicarbazide solution (1.0% (w/v) semicarbazide hydrochloride and 1.5% (w/v) sodium acetate dissolved in distilled water) was added and incubated at 30° C. for 15 min. The final reaction mixture was diluted with 500 µl distilled water and then measured at 250 nm. The absorbance coefficient of the semicarbazone formation toward 2-keto-3-deoxy gluconate (KDG) was taken to be $0.571 \times 10^3$ $M^{-1}$ $cm^{-1}$.

TBA assay was performed as follows: the reaction mixtures of 50 μl were oxidized by 125 μl of 25 mM periodic acid in 0.25 M $H_2SO_4$ at room temperature for 20 min. To terminate oxidation, 250 μl of 2% (w/v) sodium arsenite dissolved in 0.5 M HCl was added to the reactants. Finally, after adding 1 ml of 0.3% TBA to the reactants, the reaction mixtures was heated at 100° C. for 10 mM. Produced red chromophore was monitored at 549 nm after adding an equal volume of DMSO. The absorbance coefficient of thiobarbituric acid chromophore toward KDG was estimated to be $0.347 \times 10^3$ $M^{-1}$ $cm^{-1}$. One unit of gluconate dehydratase was the amount of the enzyme producing 1 μmol of 2-keto-3-deoxy gluconate per min. from gluconate under this assay conditions. All enzyme activities were determined in three plicate.

Example 4

Identification of the Gene Encoding Gluconate Dehydratase Through N-Terminus Sequencing To analyze N-terminal sequencing, purified protein was loaded on an SDS-PAGE, blotted onto a PVDF membrane, and excised. The N-terminal sequence of gluconate dehydratase purified from S. solfataricus was determined by Edman degradation to be MRIREIEPIV. The deduced amino acid sequence (SEQ ID NO: 2) of gluconate dehydratase was exactly in agreement with SSO3198, which coded for the 45-kDa protein in the S. solfataricus P2 genome database. The predicted protein size in the genomic database corresponded to the single band of purified enzyme in the denaturing gel. Consequently, this purified protein is gluconate dehydratase, and the ORF annotated by SSO3198 is the gene, which was named gnh, encoding gluconate dehydratase in S. solfataricus.

Example 5

Characterizing Ss Gluconate Dehydratase 5-1. Substrate Specificities

For analysis of substrate specificities of gluconate dehydrates, a 10 mM solution of each aldonic acid containing carbon chains ranging from $C_4$ to $C_7$ were incubated together with 40 μg/mL of purified protein. The amount of product formation was measured by the semicarbazide method, which showed 100% conversion for D-gluconate after in incubation under the standard condition. Substrate specificity of gluconate dehydratase for sugar acids was determined by the method measuring 2-keto-3-deoxy analogues yielded from aldonic acids. Sugar acids tested are as follows: D-gluconate, D-galactonate, D-galactoheptonate, D,L-arabonate, D-glucuronate, D,L-gulonate, D,L-tartarate, D-glucarate, D,L-isovalerate, L-threonate, D-ribonate, D-galactarate, D-xylonate, D-galacturonate, D-glucitol, D-mannonate, and D,L-glycerate. Kinetic parameters for gluconate dehydratase were determined using D-gluconate (0.1 to 40 mM). All experiments were performed in three plicate.

The results of Ss gluconate dehydratase activity for the aldonic acids are shown in Table 2. The Ss gluconate dehydratase showed higher selectivity to D-gluconate than any other adonic acids. D-Galactonate and D-galactoheptonate could be used as substrates for the enzyme. Negligible but detectable activities (less than 1% of activity toward D-gluconate) were observed for the following substrates: D-glucuronate, L-gulonate, D-tartarate, D-glucarate, L-isovalerate, L-threonate, D-ribonate, L-tartarate, D-gulonate, and D-galactarate. It therefore appears that the enzyme has a preference to D-gluconate.

TABLE 2

| Substrates | Relative activity (%) | Probable structure of dehydration products |
| --- | --- | --- |
| D-Gluconate | 100.0 | 2-keto-3-deoxy-D-gluconate |
| D-Galactonate | 2.8 | 2-keto-3-deoxy-D-galactonate |
| D-Galactoheptonate | 1.6 | 2-keto-3-deoxy-D-galactoheptonate |
| D-Arabonate | 0.7 | 2-keto-4,5-dihydroxy-D-valeric acid |

Less than 1% activity on the following substrates; D-glucuronate (0.65), L-gulonate (0.41), D-tartarate (0.41), D-glucarate (0.32) D, L-isovalerate (0.25), L-threonate (0.16), D-ribonate (0.16), L-tartarate (0.16), D-gulonate (0.16), and D-galactarate (0.10).
No reaction on the following substrates: L-arabonate, D-xylonate, D-galacturonate, D-glucitol, D-mannonate, and D, L-glycerate.
The relative enzyme activity was assayed by measuring the 2-keto-3-deoxy analogues produced from 10 mM each of aldonic acid containing 1 mM $CoCl_2$ in 50 mM Tri-HCl buffer (pH 7.0) for 30 min at 78?C. using the semicarbazide method.

Biochemical and kinetic parameters for the enzyme were determined using the assay method described above under standard conditions.

5-2. Kinetic Parameters

Values for $V_{max}$ and $K_m$ were determined from Lineweaver bulk plots. The rate dependence on substrate concentration followed Michaelis-Meten kinetics. From Lineweaver-Burk plots, $K_m$ and $V_m$ values of 16.7 mM and 34.5 units/mg were determined with D-gluconate as the substrate. The turnover number ($k_{cat}$) was calculated as 333 $s^{-1}$ for gluconate dehydratase, and the value of $k_{cat}/K_m$ was 19.9.

5-3. Optimum Temperature

Figure 3:
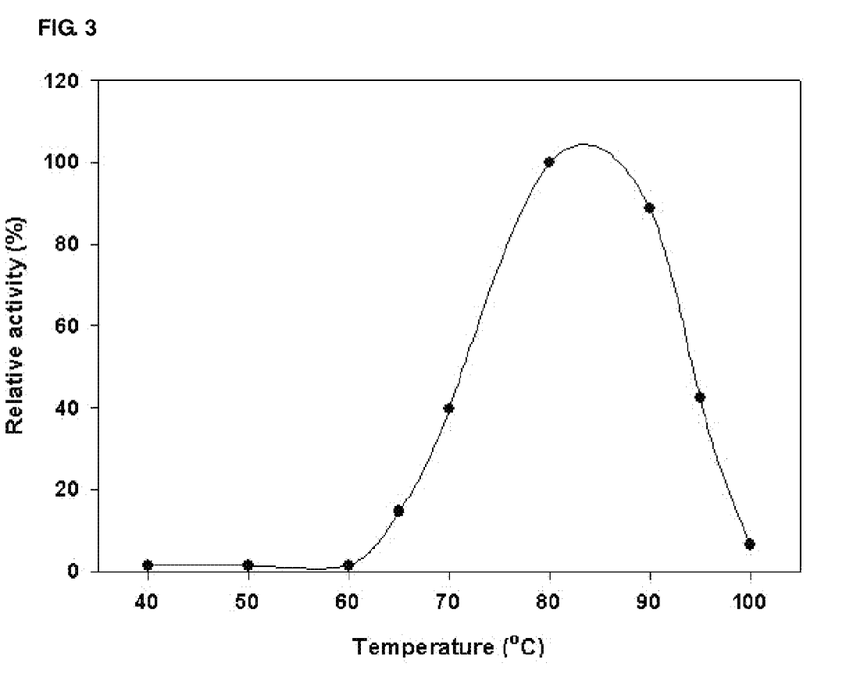
FIG. 3 shows an effect of temperature on the activity of gluconate dehydratase from *S. solfataricus*.

The temperature profile for enzyme activity was determined between 40 and 100° C. FIG. 3 shows an effect of temperature on the activity of gluconate dehydratase from S. solfataricus. The purified gluconate dehydratase displayed optimal activity between 80 and 90° C. Enzyme activity was not detectable below 60° C.

5-4. Thermostability

Enzyme thermostability was determined at 80, 90, and 100° C. by incubating enzyme solution (50 μg/ml) in 50 mM Tri-HCl (pH 7.2). At an appropriate time, samples were taken and completely cooled on ice and then measured for residual activities under standard conditions. The thermostability of purified gluconate dehydrates was measured at 80, 90, and 100° C. At 80° C., the optimal temperature for growth of S. solfataricus P2, the gluconate dehydratase was very stable over 2 hours. At 90° C., enzyme activity decreased below 50% after a 2 hour incubation. At 100° C., however, the enzyme had a half-life of less than 40 min.

5-5. Optimum pH

The effect of pH on gluconate dehydratase activity was determined at 78° C. in a citric acid-NaOH buffer (pH 2.7-5.0), 50 mM Tris-HCl buffer (pH 5.8-8.0), and 50 mM glycine-NaOH buffer (pH 8.5-10.5).

Figure 4:
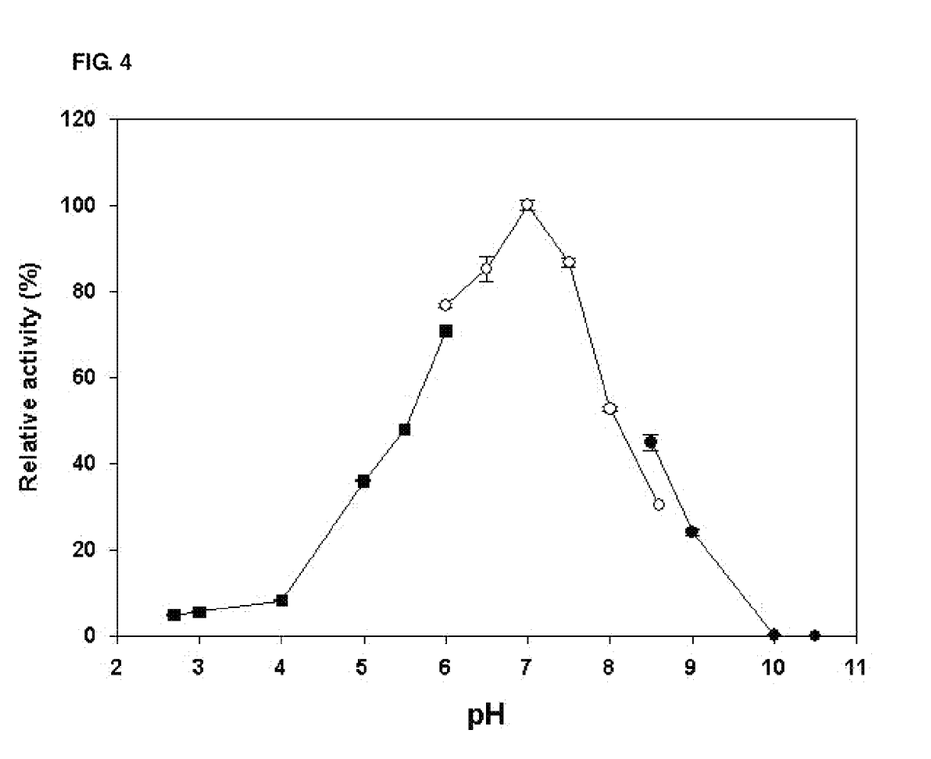
FIG. 4 shows an effect of pH on gluconate dehydratase activity.

FIG. 4 shows an effect of pH on gluconate dehydratase activity; 50 mM citric acid-NaOH (■), 50 mM Tris-HCl (●), and 50 mM glycine-NaOH buffer (○). In FIG. 4, within the pH range from pH 2.7 to pH 10.5, the activity of purified enzyme displayed an optimum between pH 7.0 to 8.0.

Example 6

Mass Determination of Native Gluconate Dehydratase

Pure Ss gluconate dehydratase (100 μg) of EXAMPLE 2 was chromatogramed through a Sephacryl S-200 column (1.0×89 cm) using the gel filtration calibration kit (Pharmacia Biotech, Sweden). The equilibrium and elution buffer used was 50 mM Tris-HCl, pH 7.2, containing 150 mM NaCl, and the flow rate was 0.5 ml/min. The molecular weight markers used were thyroglobulin (669 kDa), ferritin (440 kDa), catalase (232 kDa), aldolase (158 kDa), BSA (67 kDa), ovalbumin (43 kDa), chymotrypsin (25 kDa), and ribonuclease A (13.7 kDa). Proteins were detected at 280 nm, and gluconate dehydratase activity was measured by the standard method. The gluconate dehydratase molecular weight was calculated by interpolation on a plot of log molecular mass against the $K_{av}$ values following the recommended procedure.

The native molecular weight of purified enzyme was 357±42 kDa, as measured on a calibrated Sephacryl S-200 column with standard molecular weight markers. The molecular mass of denaturated gluconate dehydratase determined from SDS-PAGE was approximately 44 kDa. These results indicate that the *S. solfataricus* gluconate dehydratase in its native conformation is an octamer consisting of eight identical subunits.

Example 7

Cloning of Gene Coding Gluconate Dehydratase from *Sulfolobus solfataricus*

7-1. Cloning

The gene coding thermostable gluconate dehydratase was cloned from the hyperthermophilic archaeon *Sulfolobus solfataricus* (Ss).

Amino terminal protein microsequencing was performed by the Korea Basic Science Institute (KBSI) (Daejeon, Korea) on 100 picomoles (pmol) of homogeneous native Ss gluconate dehydratase prepared as described in Example 2. The sequence of the 10 N-terminal amino acid residues thereby obtained was later shown to correspond exactly with deduced residues shown in SEQ ID NO 4 from residue 1 to residue 10.

DNA encoding the Ss gluconate dehydratase of the present invention, SEQ ID NO 1, was initially amplified from *Sulfolobus solfataricus* genomic DNA by the PCR technique using the primer set of SEQ ID NO:5 and 6, including the BamHI restriction site and HindIII restriction site. The amplified fragments were inserted into the BamHI and HindIII sites of pGEM-T easy (Promega, USA) and the resulting vector was digested by each BamHI and HindIII restriction enzyme. The 1,188 bp fragments were ligated into the BamHI and HindIII sites of pRSET vector (Invitrogen, USA) including antibiotic resistance ($Amp^r$), a bacterial origin of replication (ori), and IPTG-regulatable promoter operator (P/O), a ribosome binding site (RBS), a 6-His tag, and restriction enzyme sites, and the resulting vector was designated as pGNH. The pGNH contains the complete 3,993 bp fragment encoding Ss gluconate dehydratase flanked at the fragment's termini by BamHI and HindIII.

The pGNH was then used to transform the *E. coli* strain BL21(DE3) which is a protease-deficient mutant to protect heterologously expressed proteins against protease. Transformants were selected by growing in LB medium supplemented with ampicillin, and were harvested to confirmed whether the gnh gene was placed therein by restriction analysis.

7-2. Expression

Transformants were grown overnight in a liquid culture in LB media supplemented with Amp (100 µg/ml). The overnight culture was used to inoculate a large culture at a ratio of 1:100 to 1:250. The cells were grown to an optical density ($OD_{600}$) of between 0.4 and 0.6. Isopropyl-β-D-thiogalactopyranoside (IPTG) was then added to a final concentration of 1 mM. IPTG induces by inactivating the lac repressor, clearing the P/O leading to increased gene expression. Cells were grown an extra 4 to 6 hours, and were then harvested by centrifugation.

Example 8

Purification of Recombinant Ss Gluconate Dehydratase

Recombinant Ss gluconate dehydrates was purified from *E. coli* containing the plasmid pGNH described in Example 7.

Cultures of *Escherichia coli* BL21(DE3)/pGNH were prepared as before, and 30 grams of cultured cells were isolated, admixed in 120 ml lysis buffer (prepared as in Example 2), and sonicated 10 times for 6 minutes each at full power. The resulting lysate was centrifuged for 30 minutes at 7,000 rpm. The supernatant from centrifugation was isolated and then placed for 20 minutes in a 90° C. water bath. The heat-denaturated solution was then centrifuged as above and the resultant was isolated and then loaded on an $IMAC^?$ column equilibrated in 50 mM Tris-HCl, pH 7.2 as described in Example 2. The column was washed with 3 column volumes of the same buffer, and then eluted with a gradient of 0-0.2 M imidazole in the same buffer, thereby collecting gradient elution fractions. The gluconate dehydratase activity assay was performed on each fraction, and peak activity fractions were pooled and dialyzed in 50 mM Tris-HCl (pH 7.2).

Following dialysis, the dialysate was loaded on a Q-Sepharose column equilibrated with 50 mM Tris-HCl, pH 7.2, as described in Example 2. The column was washed with 3 column volumes and eluted with a 0-1.0 M NaCl gradient in 50 mM Tris-HCl (pH 7.2). Peak activity fractions were pooled and assayed, and active fractions were pooled and concentrated 10-20 fold in a Vivaspin™ concentrator (Vivascience, Lincoln, UK). The concentrated pool was then dialyzed against a final dialysis buffer to form purified recombinant Ss gluconate dehydratase.

The activity of the recombinant Ss gluconate dehydratase was determined by the method described in Example 3.

Example 9

Dehydration of Gluconic Acid to 2-Keto-3-deoxy Gluconate by Recombinant Gluconate Dehydratase The recombinant gluconate dehydratase from *S. solfataricus* was used for the dehydration of gluconic acid to 2-keto-3-deoxy gluconate.

Figure 5:
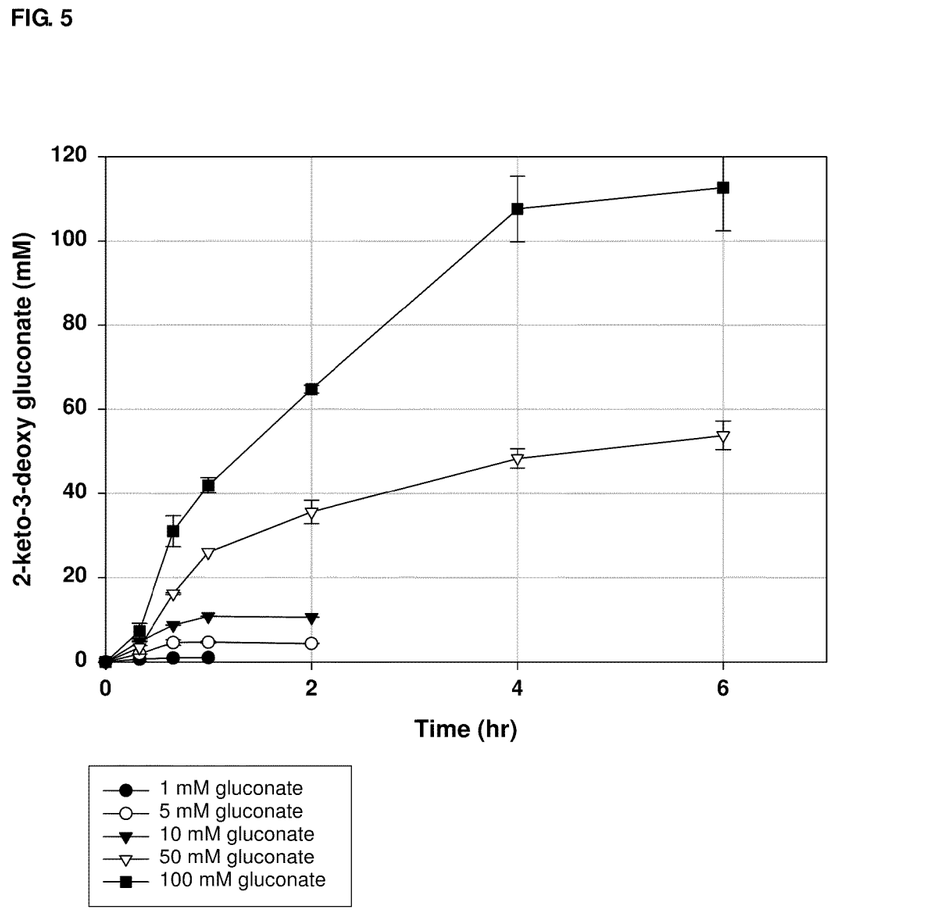
FIG. 5 is graph showing conversion result of 2-keto-3-deoxy gluconate from the gluconic acid when the Ss gluconate dehydratase was reacted to at pH 8.0 and 78° C. for 6 h

The reaction mixture consisted of 1, 5, 10, 50, and 100 mM gluconic acid sodium salt (Sigma Chemical Co., St. Louis, Mo., USA), and the Ss gluconate dehydratase in 50 mM Tris-HCl buffer (pH 8.0). The gluconate dehydratase was added at a concentration of 3.5 mg/ml, and the reaction was carried out at 78° C. for 6 hours. 2-Keto-3-deoxy gluconate was assayed by the standard procedure described in Example 3. 2-Keto-3-deoxy gluconate was produced by the Ss gluconate dehydratase as shown in FIG. 5.

The optimum conditions of recombinant Ss gluconate dehydratase for dehydrating aldonic acid to 2-keto-3-deoxy aldonic acid follow:

Enzyme concentration: 0.1-1 mg/mL
Substrate concentration: 100-200 mM
Reaction time: within 6 hours
Temperature: about 80° C.
pH: 7.5-8.0

SEQUENCE LIST TEXT

SEQ ID NO:1—Open Reading Frame encoding gluconate dehydratase from *Sulfolobus solfataricus*.
SEQ ID NO:2—amino acid sequence of gluconate dehydratase from *Sulfolobus* solfataricus.
SEQ ID NO:3—nucleic acid sequence of pGNH vector.
SEQ ID NO:4—N-terminal amino acid sequence from the gluconate dehydratase purified from *Sulfolobus solfataricus*.
SEQ ID NO:5—nucleic acid sequence of sense primer with BamHI restriction site.
SEQ ID NO:6—nucleic acid sequence of antisense primer with HindIII restriction site.

The invention claimed is:

1. A method for producing a 2-keto-3-deoxy aldonic acid from aldonic acid, comprising: contacting a gluconate dehydratase to aldonic acid in water or an aqueous solvent at a temperature from 0° C. to 120° C. and a pH of 1.5 to 12, wherein the mixing ratio of gluconate dehydratase to aldonic acid is 1 ug: 0.01 to 1 mol, and the gluconate dehydratase consists of the amino acid sequence of SEQ ID NO: 2; and isolating the 2-keto-3-deoxy aldonic acid.

2. The method according to claim 1, wherein the gluconate dehydratase is selected from the group consisting of an isolated native gluconate dehydratase, a chemically synthesized gluconate dehydratase, and a recombinant gluconate dehydratase.

3. The method according to claim 2, wherein the gluconate dehydratase is a recombinant gluconate dehydratase expressed by *Escherichia coli* BL21(DE3)/pGNH (KCTC10619BP).

4. The method according to claim 1, wherein the aldonic acid is selected from the group consisting of D-gluconate, D-Galactonate, D-Galactoheptonate, D-Arabonate, D-glucuronate, L-gulonate, D-tartarate, D-glucarate, L-isovalerate, L-threonate, D-ribonate, L-tartarate, D-gulonate, and D-galactarate.

* * * * *

```
                         SEQUENCE LISTING

<160> NUMBER OF SEQ ID NOS: 6

<210> SEQ ID NO 1
<211> LENGTH: 1189
<212> TYPE: DNA
<213> ORGANISM: Sulfolobus solfataricus
<220> FEATURE:
<221> NAME/KEY: CDS
<222> LOCATION: (1)..(1185)
<223> OTHER INFORMATION: Open Reading Frame encoding gluconate
      dehydratase

<400> SEQUENCE: 1 atg aga atc aga gaa ata gaa cca ata gta ctc acc tcg aaa gag aaa        48
Met Arg Ile Arg Glu Ile Glu Pro Ile Val Leu Thr Ser Lys Glu Lys
  1               5                  10                  15 gga agt gca act tgg gca tct ata atg att gtc aca agg gtc att acg        96
Gly Ser Ala Thr Trp Ala Ser Ile Met Ile Val Thr Arg Val Ile Thr
             20                  25                  30 gaa aat ggg gaa gta ggc tat ggt gag gca gta ccc aca cta aga gtt       144
Glu Asn Gly Glu Val Gly Tyr Gly Glu Ala Val Pro Thr Leu Arg Val
         35                  40                  45 ata tct gta tat aac gca att aaa caa gtt agt aag gct tat ata ggg       192
Ile Ser Val Tyr Asn Ala Ile Lys Gln Val Ser Lys Ala Tyr Ile Gly
     50                  55                  60 aaa gag gta gag gaa gtt gag aag aac tat cat gaa tgg tat aaa caa       240
Lys Glu Val Glu Glu Val Glu Lys Asn Tyr His Glu Trp Tyr Lys Gln
 65                  70                  75                  80 gat ttc tat tta gct agg tct ttt gaa tca gca act gca gta agt gca       288
Asp Phe Tyr Leu Ala Arg Ser Phe Glu Ser Ala Thr Ala Val Ser Ala
                 85                  90                  95 atc gat ata gcc tca tgg gat ata ata ggg aaa gag ctt gga gca cca       336
Ile Asp Ile Ala Ser Trp Asp Ile Ile Gly Lys Glu Leu Gly Ala Pro
            100                 105                 110 att cat aaa tta tta gga gga aaa acc agg gat agg gta cca gtc tac       384
Ile His Lys Leu Leu Gly Gly Lys Thr Arg Asp Arg Val Pro Val Tyr
        115                 120                 125 gca aac gga tgg tat cag gac tgc gta act cca gag gaa ttt gcg gaa       432
Ala Asn Gly Trp Tyr Gln Asp Cys Val Thr Pro Glu Glu Phe Ala Glu
    130                 135                 140 aag gca aaa gac gtt gta aag atg gga tat aag gct tta aaa ttt gat       480
Lys Ala Lys Asp Val Val Lys Met Gly Tyr Lys Ala Leu Lys Phe Asp
145                 150                 155                 160 ccg ttt ggt cca tat tac gat tgg ata gat gag aga ggt cta aga gaa       528
Pro Phe Gly Pro Tyr Tyr Asp Trp Ile Asp Glu Arg Gly Leu Arg Glu
                165                 170                 175 gct gag gag aga gta aag gct gtt aga gag gca gtt gga gac aac gtg       576
Ala Glu Glu Arg Val Lys Ala Val Arg Glu Ala Val Gly Asp Asn Val
            180                 185                 190 gat att tta ata gag cat cac ggt agg ttt aat gcg aat tcg gct att       624
Asp Ile Leu Ile Glu His His Gly Arg Phe Asn Ala Asn Ser Ala Ile
        195                 200                 205 atg ata gcg aaa aga ttg gaa aaa tac aat ccg gga ttt atg gag gaa       672
Met Ile Ala Lys Arg Leu Glu Lys Tyr Asn Pro Gly Phe Met Glu Glu
```

```
                210                 215                 220
ccg gta cat cat gag gac gta att ggt tta aga aag tat aaa gcc agt       720
Pro Val His His Glu Asp Val Ile Gly Leu Arg Lys Tyr Lys Ala Ser
225                 230                 235                 240 act cat tta agg gtt gca ttg gga gaa aga ctg ata agt gaa aag gaa       768
Thr His Leu Arg Val Ala Leu Gly Glu Arg Leu Ile Ser Glu Lys Glu
                245                 250                 255 act gcg ttt tac gtt gag gaa ggt ctt gta aac ata ttg caa cca gat       816
Thr Ala Phe Tyr Val Glu Glu Gly Leu Val Asn Ile Leu Gln Pro Asp
            260                 265                 270 tta act aat ata ggt ggt gta aca gta ggt agg agt gtt ata aaa ata       864
Leu Thr Asn Ile Gly Gly Val Thr Val Gly Arg Ser Val Ile Lys Ile
        275                 280                 285 gct gaa gct aat gat gta gag gtg gct ttt cac aac gcc ttt ggt tca       912
Ala Glu Ala Asn Asp Val Glu Val Ala Phe His Asn Ala Phe Gly Ser
    290                 295                 300 ata cag aat gca gtt gaa ata caa cta agt gca gtt aca cag aat ttg       960
Ile Gln Asn Ala Val Glu Ile Gln Leu Ser Ala Val Thr Gln Asn Leu
305                 310                 315                 320 tat tta ctt gag aac ttc tat gat tgg ttc cct cag tgg aaa agg gat      1008
Tyr Leu Leu Glu Asn Phe Tyr Asp Trp Phe Pro Gln Trp Lys Arg Asp
                325                 330                 335 tta gta tat aat gaa acg cca gtt gaa gga ggt cac gtt aag gtt cca      1056
Leu Val Tyr Asn Glu Thr Pro Val Glu Gly Gly His Val Lys Val Pro
            340                 345                 350 tac aag cct gga cta ggt gtt tca att aat gaa aaa ata ata gaa cag      1104
Tyr Lys Pro Gly Leu Gly Val Ser Ile Asn Glu Lys Ile Ile Glu Gln
        355                 360                 365 cta aga gct gaa cca ata cca tta gat gta att gaa gaa ccg gtt tgg      1152
Leu Arg Ala Glu Pro Ile Pro Leu Asp Val Ile Glu Glu Pro Val Trp
    370                 375                 380 gtc gtc aag gga acc tgg aag aat tat ggt gtt         tgaa              1189
Val Val Lys Gly Thr Trp Lys Asn Tyr Gly Val
385                 390                 395

<210> SEQ ID NO 2
<211> LENGTH: 395
<212> TYPE: PRT
<213> ORGANISM: Sulfolobus solfataricus

<400> SEQUENCE: 2

Met Arg Ile Arg Glu Ile Glu Pro Ile Val Leu Thr Ser Lys Glu Lys
1               5                   10                  15

Gly Ser Ala Thr Trp Ala Ser Ile Met Ile Val Thr Arg Val Ile Thr
            20                  25                  30

Glu Asn Gly Glu Val Gly Tyr Gly Glu Ala Val Pro Thr Leu Arg Val
        35                  40                  45

Ile Ser Val Tyr Asn Ala Ile Lys Gln Val Ser Lys Ala Tyr Ile Gly
    50                  55                  60

Lys Glu Val Glu Glu Val Lys Asn Tyr His Glu Trp Tyr Lys Gln
65                  70                  75                  80

Asp Phe Tyr Leu Ala Arg Ser Phe Glu Ser Ala Thr Ala Val Ser Ala
                85                  90                  95

Ile Asp Ile Ala Ser Trp Asp Ile Ile Gly Lys Glu Leu Gly Ala Pro
            100                 105                 110

Ile His Lys Leu Leu Gly Gly Lys Thr Arg Asp Arg Val Pro Val Tyr
        115                 120                 125

Ala Asn Gly Trp Tyr Gln Asp Cys Val Thr Pro Glu Glu Phe Ala Glu
    130                 135                 140
```

Lys Ala Lys Asp Val Val Lys Met Gly Tyr Lys Ala Leu Lys Phe Asp
145                 150                 155                 160

Pro Phe Gly Pro Tyr Tyr Asp Trp Ile Asp Glu Arg Gly Leu Arg Glu
            165                 170                 175

Ala Glu Glu Arg Val Lys Ala Val Arg Glu Ala Val Gly Asp Asn Val
        180                 185                 190

Asp Ile Leu Ile Glu His His Gly Arg Phe Asn Ala Asn Ser Ala Ile
    195                 200                 205

Met Ile Ala Lys Arg Leu Glu Lys Tyr Asn Pro Gly Phe Met Glu Glu
    210                 215                 220

Pro Val His His Glu Asp Val Ile Gly Leu Arg Lys Tyr Lys Ala Ser
225                 230                 235                 240

Thr His Leu Arg Val Ala Leu Gly Glu Arg Leu Ile Ser Glu Lys Glu
            245                 250                 255

Thr Ala Phe Tyr Val Glu Glu Gly Leu Val Asn Ile Leu Gln Pro Asp
            260                 265                 270

Leu Thr Asn Ile Gly Gly Val Thr Val Gly Arg Ser Val Ile Lys Ile
    275                 280                 285

Ala Glu Ala Asn Asp Val Glu Val Ala Phe His Asn Ala Phe Gly Ser
290                 295                 300

Ile Gln Asn Ala Val Glu Ile Gln Leu Ser Ala Val Thr Gln Asn Leu
305                 310                 315                 320

Tyr Leu Leu Glu Asn Phe Tyr Asp Trp Phe Pro Gln Trp Lys Arg Asp
            325                 330                 335

Leu Val Tyr Asn Glu Thr Pro Val Glu Gly His Val Lys Val Pro
            340                 345                 350

Tyr Lys Pro Gly Leu Gly Val Ser Ile Asn Glu Lys Ile Ile Glu Gln
        355                 360                 365

Leu Arg Ala Glu Pro Ile Pro Leu Asp Val Ile Glu Glu Pro Val Trp
    370                 375                 380

Val Val Lys Gly Thr Trp Lys Asn Tyr Gly Val
385                 390                 395

<210> SEQ ID NO 3
<211> LENGTH: 4050
<212> TYPE: DNA
<213> ORGANISM: Sulfolobus solfataricus
<220> FEATURE:
<221> NAME/KEY: gene
<222> LOCATION: (208)..(1396)
<223> OTHER INFORMATION: Open Reading Frame encoding gluconate
      dehydratase from Sulfolobus solfataricus
<220> FEATURE:
<221> NAME/KEY: promoter
<222> LOCATION: (20)..(32)
<223> OTHER INFORMATION: T7 promoter
<220> FEATURE:
<221> NAME/KEY: gene
<222> LOCATION: (100)..(207)
<223> OTHER INFORMATION: His-tag fusion region
<220> FEATURE:
<221> NAME/KEY: gene
<222> LOCATION: (2149)..(2963)
<223> OTHER INFORMATION: Ampicillin resistance gene

<400> SEQUENCE: 3
gatctcgatc cgcgaaatt aatacgactc actataggga gaccacaacg gtttccctct      60
agaaataatt ttgtttaact ttaagaagga gatatacata tgcggggttc tcatcatcat     120
catcatcatg gtatggctag catgactggt ggacagcaaa tgggtcggga tctgtacgac     180

```
gatgacgata aggatcgatg gggatccatg agaatcagag aaatagaacc aatagtactc      240
acctcgaaag agaaaggaag tgcaacttgg gcatctataa tgattgtcac aagggtcatt      300
acggaaaatg gggaagtagg ctatggtgag gcagtaccca cactaagagt tatatctgta      360
tataacgcaa ttaaacaagt tagtaaggct tatataggga aagagggtaga ggaagttgag      420 aagaactatc atgaatggta taaacaagat ttctatttag ctaggtcttt tgaatcagca      480
actgcagtaa gtgcaatcga tatagcctca tgggatataa tagggaaaga gcttggagca      540
ccaattcata aattattagg aggaaaaacc agggataggg taccagtcta cgcaaacgga      600
tggtatcagg actgcgtaac tccagaggaa tttgcggaaa aggcaaaaga cgttgtaaag      660
atgggatata aggctttaaa atttgatccg tttggtccat attacgattg gatagatgag      720
agaggtctaa gagaagctga ggagagagta aaggctgtta gagaggcagt tggagacaac      780
gtggatattt taatagagca tcacggtagg tttaatgcga attcggctat tatgatagcg      840
aaaagattgg aaaaatacaa tccgggattt atggaggaac cggtacatca tgaggacgta      900
attggtttaa gaaagtataa agccagtact catttaaggg ttgcattggg agaaagactg      960
ataagtgaaa aggaaactgc gttttacgtt gaggaaggtc ttgtaaacat attgcaacca     1020
gatttaacta atataggtgg tgtaacagta ggtaggagtg ttataaaaat agctgaagct     1080
aatgatgtag aggtggcttt tcacaacgcc tttggttcaa tacagaatgc agttgaaata     1140
caactaagtg cagttacaca gaatttgtat ttacttgaga acttctatga ttggttccct     1200
cagtggaaaa gggatttagt atataatgaa acgccagttg aaggaggtca cgttaaggtt     1260
ccatacaagc ctggactagg tgtttcaatt aatgaaaaaa taatagaaca gctaagagct     1320
gaaccaatac cattagatgt aattgaagaa ccggtttggg tcgtcaaggg aacctggaag     1380
aattatggtg tttgaaagct tgatccggct gctaacaaag cccgaaagga agctgagttg     1440
gctgctgcca ccgctgagca ataactagca taaccccttg gggcctctaa acgggtcttg     1500 agggttttt tgctgaaagg aggaactata tccggatctg gcgtaatagc gaagaggccc     1560
gcaccgatcg cccttcccaa cagttgcgca gcctgaatgg cgaatgggac gcgccctgta     1620
gcggcgcatt aagcgcggcg ggtgtggtgg ttacgcgcag cgtgaccgct acacttgcca     1680
gcgccctagc gcccgctcct ttcgctttct tcccttcctt tctcgccacg ttcgccggct     1740
ttccccgtca gctctaaat cggggggctcc ctttagggtt ccgatttagt gctttacggc     1800
acctcgaccc caaaaaactt gattaggtg atggttcacg tagtgggcca tcgccctgat     1860
agacggtttt tcgccctttg acgttggagt ccacgttctt taatagtgga ctcttgttcc     1920
aaactggaac aacactcaac cctatctcgg tctattcttt tgatttataa gggattttgc     1980
cgatttcggc ctattggtta aaaatgagc tgatttaaca aaaatttaac gcgaatttta     2040
acaaaatatt aacgcttaca atttaggtgg cacttttcgg ggaaatgtgc gcggaacccc     2100
tatttgttta ttttctaaa tacattcaaa tatgtatccg ctcatgagac aataaccctg     2160
ataaatgctt caataatatt gaaaaaggaa gagtatgagt attcaacatt tccgtgtcgc     2220
ccttattccc ttttttgcgg catttttgcct tcctgtttt tgctcacccag aaacgctggt     2280 gaaagtaaaa gatgctgaag atcagttggg tgcacgagtg ggttacatcg aactggatct     2340
caacagcggt aagatccttg agagttttcg ccccgaagaa cgttttccaa tgatgagcac     2400
ttttaaagtt ctgctatgtg gcgcggtatt atcccgtatt gacgccgggc aagagcaact     2460
cggtcgccgc atacactatt ctcagaatga cttggttgag tactcaccag tcacagaaaa     2520
gcatcttacg gatggcatga cagtaagaga attatgcagt gctgccataa ccatgagtga     2580
```

```
taacactgcg gccaacttac ttctgacaac gatcggagga ccgaaggagc taaccgcttt      2640
tttgcacaac atgggggatc atgtaactcg ccttgatcgt tgggaaccgg agctgaatga      2700
agccatacca aacgacgagc gtgacaccac gatgcctgta gcaatggcaa caacgttgcg      2760
caaactatta actggcgaac tacttactct agcttcccgg caacaattaa tagactggat      2820
ggaggcggat aaagttgcag gaccacttct gcgctcggcc cttccggctg ctggttttat      2880
tgctgataaa tctggagccg gtgagcgtgg gtctcgcggt atcattgcag cactggggcc      2940
agatggtaag ccctcccgta tcgtagttat ctacacgacg gggagtcagg caactatgga      3000
tgaacgaaat agacagatcg ctgagatagg tgcctcactg attaagcatt ggtaactgtc      3060
agaccaagtt tactcatata tactttagat tgatttaaaa cttcattttt aatttaaaag      3120
gatctaggtg aagatccttt ttgataatct catgaccaaa atcccttaac gtgagttttc      3180
gttccactga gcgtcagacc ccgtagaaaa gatcaaagga tcttcttgag atcctttttt      3240
tctgcgcgta atctgctgct tgcaaacaaa aaaaccaccg ctaccagcgg tggtttgttt      3300
gccggatcaa gagctaccaa ctcttttttcc gaaggtaact ggcttcagca gagcgcagat      3360
accaaatact gttcttctag tgtagccgta gttaggccac cacttcaaga actctgtagc      3420
accgcctaca tacctcgctc tgctaatcct gttaccagtg gctgctgcca gtggcgataa      3480
gtcgtgtctt accgggttgg actcaagacg atagttaccg gataaggcgc agcggtcggg      3540
ctgaacgggg ggttcgtgca cacagcccag cttggagcga acgacctaca ccgaactgag      3600
atacctacag cgtgagctat gagaaagcgc cacgcttccc gaaggagaa aggcggacag      3660 gtatccggta agcggcaggg tcggaacagg agagcgcacg agggagcttc caggggggaaa      3720 cgcctggtat ctttatagtc ctgtcgggtt tcgccacctc tgacttgagc gtcgattttt      3780
gtgatgctcg tcagggggc ggagcctatg gaaaaacgcc agcaacgcgg cctttttacg      3840
gttcctggcc ttttgctggc cttttgctca catgttcttt cctgcgttat ccccctgattc      3900 tgtggataac cgtattaccg cctttgagtg agctgatacc gctcgccgca gccgaacgac      3960
cgagcgcagc gagtcagtga gcgaggaagc ggaagagcgc ccaatacgca aaccgcctct      4020
ccccgcgcgt tggccgattc attaatgcag                                       4050
```

```
<210> SEQ ID NO 4
<211> LENGTH: 10
<212> TYPE: PRT
<213> ORGANISM: Sulfolobus solfataricus
<220> FEATURE:
<221> NAME/KEY: PEPTIDE
<222> LOCATION: (1)..(10)
<223> OTHER INFORMATION: N-terminal amino acid sequence from the
      gluconate dehydratase purified from Sulfolobus solfataricus

<400> SEQUENCE: 4

Met Arg Ile Arg Glu Ile Glu Pro Ile Val
  1               5                  10

<210> SEQ ID NO 5
<211> LENGTH: 30
<212> TYPE: DNA
<213> ORGANISM: Artificial Sequence
<220> FEATURE:
<223> OTHER INFORMATION: sense primer with BamHI restriction site

<400> SEQUENCE: 5
cgggatccat gagaatcaga gaaatagaac                                         30

<210> SEQ ID NO 6
```

```
<211> LENGTH: 28
<212> TYPE: DNA
<213> ORGANISM: Artificial Sequence
<220> FEATURE:
<223> OTHER INFORMATION: antisense primer with HindIII restriction site

<400> SEQUENCE: 6
cccaagcttt caaacaccat aattacag                                              28
```